United States Patent [19]

Faggian et al.

[11] Patent Number: 4,607,121

[45] Date of Patent: Aug. 19, 1986

[54] PROCESS FOR PREPARING ALKALINE METAL SALTS OF POLYETHOXYCARBOXYLIC ACIDS

[75] Inventors: Lucio Faggian, S. Donato Milanese; Renato de Simone, Como; Edoardo Platone, S. Donato Milanese, all of Italy

[73] Assignee: AGIP, S.p.A., Rome, Italy

[21] Appl. No.: 682,907

[22] Filed: Dec. 18, 1984

[30] Foreign Application Priority Data

Dec. 28, 1983 [IT] Italy ............................. 24409 A/83

[51] Int. Cl.$^4$ .......................................... C07C 51/235
[52] U.S. Cl. ...................................... 562/537; 502/24
[58] Field of Search ...................... 562/538, 537, 539; 502/339, 24

[56] References Cited

U.S. PATENT DOCUMENTS

| | | | |
|---|---|---|---|
| 3,449,413 | 6/1969 | Hartel et al. | 562/538 |
| 3,595,909 | 7/1971 | Sheldon | 562/538 |
| 3,739,020 | 6/1973 | McClain et al. | 562/538 |
| 3,799,977 | 3/1974 | Rutledge | 562/538 |
| 3,929,873 | 12/1975 | Gammans | 562/537 |
| 4,214,101 | 7/1980 | Miya et al. | 562/537 |
| 4,233,460 | 11/1980 | Willis et al. | 562/537 |
| 4,256,916 | 3/1981 | Morris et al. | 562/537 |

FOREIGN PATENT DOCUMENTS

| | | | |
|---|---|---|---|
| 747424 | 11/1966 | Canada | 562/537 |
| 2407146 | 9/1975 | Fed. Rep. of Germany | 562/538 |
| 2945961 | 6/1981 | Fed. Rep. of Germany | 502/24 |
| 383113 | 9/1957 | Japan | 562/537 |
| 534633 | 3/1941 | United Kingdom | 562/538 |
| 1068128 | 5/1967 | United Kingdom | 562/538 |
| 1089134 | 11/1967 | United Kingdom | 562/538 |
| 2010248 | 6/1979 | United Kingdom | 562/537 |

OTHER PUBLICATIONS

Mills, *Kirk–Othmer Encyclopedia of Chemical Technology*, 2nd ed., vol. 4, pp. 566, 570, 571, 586, (1964).

*Primary Examiner*—Natalie Trousof
*Assistant Examiner*—Bruce D. Gray
*Attorney, Agent, or Firm*—Hedman, Gibson, Costigan & Hoare

[57] ABSTRACT

A process for preparing an alkaline metal salt of a polyethoxycarboxylic acid defined by the formula $$R'(OR)_m(OCH_2CH_2)_{n-1}(OCH_2)COOM$$

by oxidation in the presence of a platinum or palladium catalyst, of a polyethoxy alcohol of the formula $$R'(OR)_m(OCH_2CH_2)_nOH,$$

followed by reactivating the catalyst in the reaction mixture and recovering in active form the insoluble and soluble catalyst fractions. The alkaline metal salts of polyethoxycarboxylic acids thus produced are useful as surfactants, which can be employed in the recovery of oil from wells of medium and high salinity.

8 Claims, No Drawings

PROCESS FOR PREPARING ALKALINE METAL SALTS OF POLYETHOXYCARBOXYLIC ACIDS

BACKGROUND OF THE INVENTION

1. Field of the Invention

The present invention relates to a process for the preparation of alkaline metal salts of polyethoxycarboxylic acids, useful as surfactant agents.

2. Background of the Related Art

A process is known in the art for the preparation of alkaline metal salts of polyethoxycarboxylic acids by means of the condensation of polyethoxylic alcohols with chloroacetic acid, or alkaline chloroacetate, in particular sodium chloroacetate, in the presence of an alkaline hydroxide, according to the reaction:

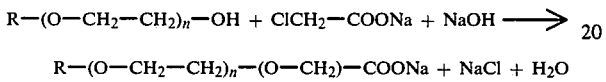

$$R-(O-CH_2-CH_2)_n-OH + ClCH_2-COONa + NaOH \longrightarrow$$
$$R-(O-CH_2-CH_2)_n-(O-CH_2)-COONa + NaCl + H_2O$$

This reaction does not arrive to its completion, or to its substantial completion, when the reactants are used in stoichiometric quantities and high conversions of the reactants are obtained only with long reaction times (of the order of 1-2 days), and using an excess of up to 50% of alkaline chloroacetate and of alkaline hydroxide, as it appears from the disclosure of German Pat. No. 2,418,444.

Together with the desired reaction product, considerable quantities are always present of alkaline glycolate and of alkaline chloride, as well as of unconverted alcohol.

Therefore, to be used, the alkaline salt of polyethoxycarboxylic acid requires a preliminary purification, and said purification is usually carried out by liberating the polyethoxycarboxylic acid from its salt by means of the treatment with a mineral acid, such as sulphuric acid and hydrochloric acid. The so separated polyethoxycarboxylic acid is then salified with alkaline hydroxide. In this treatment, the reaction byproducts, such as the alkaline glycolate and the alkaline chloride, are, separated by being dissolved in the aqueous phase during the treatment with mineral acid.

The unconverted polyethoxylic alcohol remains, on the contrary, inside the organic phase, together with the polyethoxycarboxylic acid. The process described, therefore, is affected by drawbacks, from the view points of complexity, conversion of the reactants into the useful reaction products and of the economic burdens.

In the art the possibility is moreover known generally of oxidating organic compounds of the type of alcohols into their correspondent carboxylic compounds, by means of the catalytic oxidation of said alcoholic compounds on catalysts of noble metals.

Such a technique has, however, had a poor commercial success, due to the difficulties deriving from the regeneration, recovery and reuse of the catalyst used for the purpose, as well as because the reaction originates often compounds at different oxidation level, with a consequent low yield in the desired useful product and the need for separation and purification treatments. Difficulties exist indeed for stopping the oxidation process at the desired level and avoiding the formation of undesired oxidated products, such as, e.g., peroxides.

OBJECTS OF THE INVENTION

It is therefore the purpose of the present invention to provide a process for producing alkaline metal salts of polyethoxycarboxylic acids which is free, or substantially free, from the drawbacks mentioned above.

In particular, it is a purpose of the present invention to provide, a process for the preparation of alkaline metal salts of polyethoxycarboxylic acids by means of the catalytic oxidation of polyethoxylic alcohols, which allows a substantially complete conversion of the polyethhoxylic alcohol, also avoiding the formation of peroxidated derivatives.

It is another purpose of the present invention to provide, such an oxidation process, in which it is possible to completely recover and reuse the catalyst, without its activity and selectivity being decreased.

Other purposes and advantages of the invention will be clear from the following disclosure.

DESCRIPTION OF THE INVENTION

In particular, according to the invention, alkaline metal salts are prepared of polyethoxycarboxylic acids which can be defined by means of the general formula:

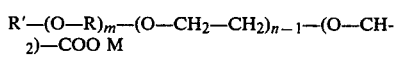

$$R'-(O-R)_m-(O-CH_2-CH_2)_{n-1}-(O-CH_2)-COO\,M$$

in which:
- R' represents an alkyl group, with linear or branched chain, containing from 1 to 20 carbon atoms, or an aryl group, optionally substituted with one or more alkyl groups, or an alkylaryl group;
- R represents an alkylene group with linear or branched chain, containing from 3 to 5 carbon atoms;
- m is a number ranging from 0 to 30;
- n is a number ranging from 2 to 30;
- M is an alkaline metal;

by means of a process which comprises:

(a) the oxidation with oxygen, or with a gas containing molecular oxygen, in the presence of a catalyst of platinum or palladium, at a temperature of from 40° to 80° C., and however lower than the cloud point of the alcohol, in an aqueous medium whose pH is controlled within the range of from 7.7 to 8.7 by means of alkaline hydroxide MeOH, of a polyethoxylic alcohol which can be defined by the general formula:

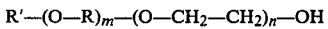

$$R'-(O-R)_m-(O-CH_2-CH_2)_n-OH$$

in which R', R, m and n have the meaning defined above; until said polyethoxylic alcohol is completely, or substantially completely, converted;

(b) the reactivation of the catalyst of platinum or of palladium, in the related reaction mixture, by treatment with gaseous hydrogen;

(c) the separation of the suspended fraction of activated catalyst and the precipitation of the fraction of activated catalyst "dissolved" in the reaction mixture, by adding to said reaction mixture a liquid aliphatic ketone, at least partly soluble in the same mixture;

(d) the separation of the precipitated activated catalyst and the recovery of the components of the reaction mixture after the catalyst has been withdrawn from it.

The alkaline metal salts of the polyethoxycarboxylic acids, which are obtained by means of the process of the present invention, are useful surfactant agents, in particular in the tertiary recovery of crude oil from medium and high salinity wells.

For such an application, the alkaline metal salts of polyethoxycarboxylic acids are preferred, having the general formula as previously reported, in which:
- R' represents an alkyl group, with linear or branched chain, containing from 6 to 20 carbon atoms, or a phenyl group, substituted with one or two alkyl linear or branched chains, containing from 6 to 8 carbon atoms;
- R represents the isopropylene or the isobutylene group;
- m varies from 0 to 20;
- n varies from 2 to 30;
- Me represents sodium or potassium.

STAGE A

According to the present invention, the oxidation of the polyethoxyl alcohol is carried out by means of oxygen, or of a gas containing molecular oxygen, e.g., air, on a catalyst of platinum or palladium, at a temperature ranging from 40° to 80° C., in an aqueous medium whose pH is controlled within the range of from 7.7 to 8.7, by means of the hydroxide of the alkaline metal corresponding to the alkaline carboxylate which is to be obtained.

Conveniently, the concentrations of the reactants are so controlled as to produce a reaction mixture containing, at the end of the reaction of oxidation, from 5 to 50% by weight of the salt of alkaline metal of the polyethoxycarboxylic acid.

Lower concentrations are possible, but not desired, due to the higher cost deriving from the subsequent evaporation of the liquid medium. Higher concentrations are to be avoided, in that they create a high viscosity reaction mixture of difficult handling. The oxidation catalyst is formed by platinum or palladium, generally supported on coal or alumina. A typical catalyst contains from 1 to 10% by weight of platinum on charcoal, and is known as charcoal-supported platinum catalyst.

The oxidation temperature is moderate and is maintained within a range of from 40° to 80° C., as a function of the polyethoxylated alcohol which one desires to oxidize. In practice, when the process is carried out batchwise, the maximum value of the temperature, in the first steps of the reaction, corresponds to the cloud point value of the polyethoxylic alcohol, i.e., the temperature at which the solubility of alcohol in water decreases (see H. Stache, Tensid-Taschenbuch 2. Ausgabe; Muenchen 1981, page 15).

As the reaction proceeds, the temperature can be increased (relatively to its initial value), always within the above specified range, in that the alkaline metal salt of the polyethoxycarboxylic acid acts as dissolving agent for the residual polyethoxylic alcohol.

The pressure of oxygen is suitably maintained within the range of from 0.1 to 4 abs. atm. when pure oxygen is used. In the case of gases containing molecular oxygen, a partial pressure of oxygen is maintained within the range of above specified values.

The oxidation reaction is carried out at a pH of from 7.7 to 8.7, by adding to the reaction mixture the alkaline hydroxide corresponding to the salt of polyethoxycarboxylic acid which is to be prepared.

With pH values lower than 7.7, a decrease is observed of the reaction rate, with values higher than 8.7, the dissolving is favoured of the catalyst inside the reaction mixture.

By operating within the pH range above defined, no byproducts are practically formed, and the consumption of oxygen and of alkaline hydroxide is nearly the stoichiometric or a substantially stoichiometric one, corresponding to the formation of the alkaline salt of the polyethoxycarboxylic acid. In particular, neither analytically appreciable quantities are formed of peroxides, nor does the oxidative degradation takes place of the subsequent ethoxyl units in the chain.

The quantity of catalyst of platinum or palladium, within certain limits, has an influence on the reaction rate, but not on the selectivity of the reaction itself. Normally weight ratios are used of the platinum or of the palladium to the polyethoxylic alcohol of from 0.002:1 to 0.02:1.

From the point of view of the reaction rate, the quality of the stirring is important.

The polyethoxylic alcohol may be added, in the batchwise reaction, either completely at the beginning of the reaction, or gradually over the course of the reaction itself, e.g., over a time of from 0.5 to 2 hours or more.

It is moreover possible to carry out the oxidation reaction as a continuous process, using if desired more reactors in series.

By operating within the range of the previously defined conditions, a practically complete conversion is obtained of the polyethoxylic alcohol, with it being transformed by 99% or more into the alkaline salt of the polyethoxycarboxylic acid. The time needed to obtain such transformations varies in function of the polyethoxyl alcohol used, and of the other reaction conditions.

Generally said reaction time is comprised within the range of from 1 to 10 hours. If desired, the reaction can be stopped at any conversion level of polyethoxylic alcohol, should mixtures be desired with a predetermined ratio of anionic/non ionic surfactant agent. In this case, the reaction time is correspondingly reduced.

STAGE B

At the end of the oxidation reaction, the reactor is thoroughly purged with an inert gas, generally with nitrogen, and the catalyst is reactivated by treating the reaction mixture with gaseous hydrogen. This treatment is continued until the consumption of hydrogen ends, which requires generally from 1 to 2 hours, the operations being normally carried out at temperature values of room temperature (20°–25° C.) or close to room temperature.

STAGE C

At the end of the treatment with hydrogen the reactor is accurately purged with an inert gas, in general with nitrogen, and the reactivated platinum or palladium catalyst results in being partly suspended as a solid in the reaction mixture, and partly "dissolved" within the same mixture. The suspended portion of the catalyst is separated and recovered by means of conventional techniques such as filtration and centrifugation. The residual liquid mixture after said separation is treated with a liquid aliphatic ketone, at least partly soluble within said mixture, in a quantity of from 1 to 10 parts by weight per each part by weight of the same mixture. Preferably acetone is used for the purpose, in quantities of from 1.2 to 2 parts by weight per each part by weight of the liquid mixture. By operating under conditions of room temperature (20°–25° C.) the complete precipitation is obtained of dissolved platinum or palladium, and said precipitated platinum or palladium can be recovered by means of the normal filtration and centrifugation techniques. In practice, after said treatment the residual platinum or palladium within the liquid mixture is of the order of from 1 to 4 parts per million, relative to the alkaline metal salt of the polyethoxycarboxylic acid present in the same mixture.

STAGE D

The two fractions of platinum or palladium thus recovered show a catalytic activity equal to that of fresh catalyst, and can be recycled directly to the stage (a) of the process of the present invention.

The residual liquid mixture after the total separation of the platinum or palladium is submitted to distillation treatments, for the purpose of separating the ketone, and the thus recovered ketone can be recycled to the stage (c) of the process of the present invention.

The residue from said distillation is practically consisting of the alkaline metal salt of the polyethoxycarboxylic acid in aqueous solution, and can be used as such in the normal uses of said surfactant agent. If one wishes to obtain an alkaline metal salt of the polyethoxycarboxylic acid in a more concentrated aqueous solution, or in a water-free form, the water can be removed partly or completely, by distillation.

The following examples are provided to illustrate the invention and are not to be construed as limiting the invention.

EXAMPLE 1

A glass flask is used, of 1,000 ml in capacity, equipped with a stirrer of the magnetically driven type, with turbine and hollow shaft for the inner recycle of the gas (supplied by the firm MEDIMEX); combined electrode glass-Thalamid (supplied by the firm SCHOTT) for the measuring of pH value at temperatures as high as 80° C.; inlets of oxygen and hydrogen, with the related calibrated burettes for measuring the quantity of the gases; nitrogen inlet; loading funnel for the aqueous solution of sodium hydroxide with pressure balancing means and venting means. The flask is also provided with an electrical jacket for the external heating.

In the flask 109 g (0.3 mole) are charged of tetra(oxy-1,2-ethanediyl)-α-dodecyl-ω-hydroxy:

$$C_{12}H_{25}-(O-CH_2-CH_2)_4-OH$$

(obtained by means of the condensation of tetraethylene glycol with 1-bromodecane), together with 700 ml of deionized water and 10 g of catalyst, of platinum supported on charcoal containing 5% by weight of platinum (supplied by the firm ENGELHARDT).

The reaction is carried out under a blanket of nitrogen, and the reaction mixture is heated at 50° C. The nitrogen is then displaced from the top of the flask with 0.56 l of oxygen, and the reactor is then put into communication with the oxygen burette, maintained under a pressure of 30–40 cm of water column above the atmospheric pressure. The pH of the mixture is adjusted at values of from 7.7 to 8.7 by adding an aqueous solution of sodium hydroxide (3 molar), contained within the loading funnel. The stirrer is then started, adjusting its speed at about 1,700 rpm. Following the start of the stirring, the absorption of oxygen starts, the pH decreases and the temperature tends to rise. The heating is then adjusted, so as to maintain the temperature between 50° and 60° C.

The pH is maintained at a value comprised within the range of from 7.7 to 8.7 by feeding the aqueous solution of sodium hydroxide. After 3 hours of reaction, the absorption of oxygen terminates and the value of pH remains stable. The consumptions of oxygen and of sodium hydroxide result to be stoichiometric relatively to the foreseeable values for the desired reaction product.

The reaction flask is then purged by feeding a flow of nitrogen, and maintaining a slight stirring. The feeding of nitrogen is interrupted, the flask is connected with the hydrogen containing burette, and the stirring rate is then increased up to about 1,800 rpm. After 2 hours the absorption of hydrogen ceases. The consumption of hydrogen is of 219 ml.

The flask is purged with nitrogen, and the catalyst is recovered by filtering under reduced pressure, with Buchner funnel and Whatman No. 42 paper filter. The filtrate has the appearance of a clear grey coloured liquid. A sample of the filtrate, centrifuged within a test-tube at 5,000 rpm, for 2 hours, does not separate any settled matters. Another sample, left standing for some days, does not show any settled matters.

The analysis for platinum carried out on the filtrate (atomic absorption method) shows a content of 2.6 ppm of platinum (18.9 ppm with reference to the carboxylated reaction product).

To 689 g of filtrate, 1,310 g of acetone are added, and the whole is accurately mixed. After about 2 hours, the precipitation is observed of a black powder, which, at the analysis by X-rays, is shown to consist of Pt and C, with a notably higher Pt/C ratio relatively to the original catalyst sample. The powder is separated by filtration on Buchner filter with Whatman No. 42 paper.

The analysis of the so obtained filtrate shows the presence of 0.045 ppm of platinum (0.83 ppm with reference to the carboxylated reaction product).

The treatment with acetone allows therefore to recover a quantity of platinum of 95.6% relative to the quantity which would otherways be lost without the treatment with acetone. The loss of platinum, therefore, relative to the quantity initially loaded, is of 0.196%.

A portion of the filtrate is distilled under atmospheric pressure by using a Vigreux distiller for recovering the acetone, and the water is then separated, always by distillation, operating under reduced pressure. An oily residue is thus obtained, practically colourless, in a quantity of 101.3 g, equal to 99% of the theoretical value. The water content of this oily residue, determined by the K. Fischer method, is of 0.83%.

From the analysis of the residue by NMR spectrometry ($^1$H and $^{13}$C), IR, TLC (plate of silica gel, eluting solvent CHCl$_3$.CH$_3$OH 6:4, development with iodine vapour) and by the determination of acidic equivalent number, after exchange on Dowex W 50×8 acidic resin, it results that the same residue is formed by the sodium salt of the tri(oxyethylene)-α-dodecyl-ω-(oxymethylene)carboxylic acid:

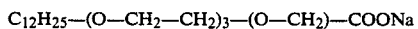

$$C_{12}H_{25}-(O-CH_2-CH_2)_3-(O-CH_2)-COONa$$

The peroxide content (as determined by the Mai-Graupner method, i.e., by means of the reduction of the peroxides with hydriodic acid in boiling acetic acid) of the carboxylate is equal to that of the starting alcoholic compound. No formation of peroxides takes place therefore during the course of the reaction of oxidation.

EXAMPLE 2

In the reaction equipment described in the preceding Example, modified with the addition of a second loading funnel, thermostatized at 50° C. and provided with the pressure balancing means, 700 g of water are charged, as well as the catalyst (platinum supported on charcoal, with 5% by weight of platinum) already used in five preceding reactions (initially charged quantity 9.0 g). In the second loading funnel, 69.15 g are introduced of the ethoxylation product of 1-dodecanol with ethylene oxide, previously purified from polyoxyethyleneglycols by extraction with ethyl acetate-brine (modified Weibull method) and from unconverted dodecanol by distillation under reduced pressure. The product which is obtained after these treatments has an average molecular weight of 363.6, has an average content of oxyethylene units of 4.02, and can be represented by the formula:

$$C_{12}H_{25}-(O-CH_2-CH_2)_{4.02}-OH.$$

The temperature inside the flask is brought to 42° C., maintaining a flow of nitrogen, and a gentle stirring of the mass. The stirring is then suspended, the flow of nitrogen is interrupted, and the flask is washed with oxygen. Inside the flask 7 ml of the hydroxylated reactant are added dropwise, and the pH is adjusted to 8.5 by means of the 2.5M aqueous solution of sodium hydroxide contained inside the other loading funnel. The reactor is put into communication with the oxygen containing burette, and the stirrer is started, adjusting its speed to 1,700–1,800 rpm.

The temperature of the reaction mixture is raised to 55° C., and is then kept constant (±1° C.) at this value. The residual portion of the reactant is then gradually fed in, over 1.75 hours, and the pH is maintained within the range of from 7.7 to 8.7 by means of the addition of the aqueous solution of sodium hydroxide. After 4 hours the oxygen is not any longer absorbed, and the pH remains constant.

The consumption of oxygen is 1.05 times the theoretical value, and that of sodium hydroxide is 1.009 times the theoretical value. The catalyst is then reactivated by operating as in Example 1. After 2.5 hours the reactivation stage is finished, and the consumption of hydrogen is of 425 ml. The filtration of the catalyst is carried out, as well as the treatment with acetone, as described in Example 1. The platinum present inside the filtrate before the treatment with acetone is 15.64 ppm (with reference to the carboxylated reaction product) and after treatment with acetone, it is 1.36 ppm. (always referred to the carboxylate). The treatment with acetone allows therefore a recovery of 91.3% of the platinum quantity, which would be lost in the absence of the treatment with acetone.

After the distillation of the solvents, the reaction product (obtained in a weight yield of 98.7% of theoretical) was characterized by means of the analytical techniques described in Example 1, and it was shown to be a mixture of sodium salts of poly(oxyethylene)-α-dodecyl-ω-(oxymethylene)carboxylic acid, with an average number of oxyethylene units per molecule of 3.12, which can therefore be represented by the formula:

$$C_{12}H_{25}-(O-CH_2-CH_2)_{3.12}-(O-CH_2)-COONa$$

The conversion of the starting alcoholic reactant is 100%. The content of peroxides of the end product is 8.8 ppm, expressed as oxygen.

EXAMPLE 3

Following the working conditions of Example 1, 27 consecutive reactions are carried out of tetra(oxyethylene)-α-dodecyl-ω-hydroxyl, using and recycling the same charge of catalyst. At the end of the tests, not any appreciable changes are observed of the activity and selectivity characteristics of the catalyst.

EXAMPLES 4–26

Following the same procedure as shown in Example 1, oxidation tests are carried out of different ethoxylated substrates.

In Table 1 the data is reported relating to said tests.

In Table 1, the symbol EO indicates the ethoxyl radical —O—CH$_2$—CH$_2$— and the number at the foot of EO indicates the ethoxylation degree, or the average ethoxylation degree.

In addition, in said Table:

(1)=Ethoxylated oxo($C_{12}$-$C_{13}$) alcohols (linearity of 42.5%).

(2)=Ethoxylated oxo($C_{12}$-$C_{13}$) alcohols (branching of 97.3%).

(3)=Ethoxylated oxo($C_{12}$-$C_{15}$) alcohols (linearity of 44.8%).

(4)=Ethoxylated oxo($C_{14}$-$C_{15}$) alcohols (linearity of 41.3%).

EXAMPLE 27

To 1 mole of 1-dodecanol, in an autoclave and in the presence of KOH as catalyst, 4.06 mole of propylene oxide are added at 150° C. When the reaction with propylene oxide is finished, 4.19 mole of ethylene oxide are added.

The resulting product is purified from the polyglycols and it is shown to have an average composition which can be represented by the formula:

$$C_{12}H_{25}-(O-CH_2-\overset{\underset{|}{CH_3}}{CH})_{4.06}-(O-CH_2-CH_2)_{4.15}-OH$$

In practice, the product is a mixture consisting of 10.68% of:

$$C_{12}H_{25}-(O-CH_2-\overset{\underset{|}{CH_3}}{CH})_{4.06}-OH$$

and consisting for the balance of:

$$C_{12}H_{25}-(O-CH_2-\overset{\underset{|}{CH_3}}{CH})_{4.06}-(O-CH_2-CH_2)_{5.57}-OH$$

From the reaction mixture 1-dodecanol is absent.

A portion of said product (150 g) is submitted to the oxidation, in the presence of 1,420 g of water and of 17 g of platinum supported on charcoal, with the 5% of platinum, according to the procedure described in example 2. The introduction time of the hydroxylated reactant is of 2 hours. The temperature is maintained to 50° C. over the course of the reaction, is raised to 60° C.

during the last part of the same reaction, and is then kept constant at that value, until the absorption of oxygen and the consumption of NaOH come to their end. The pH is always maintained within a range of from 7.7 to 8.7.

The reaction mixture is then submitted to the treatment with hydrogen; the catalyst is separated by filtration; the filtrate is treated with 1.5 parts by weight of acetone per each part by weight of the same filtrate and the day after, the precipitate obtained is separated. The platinum present within the aqueous filtrate before the treatment with acetone is of 118 ppm (relative to the carboxylated reaction product) and after the treatment with acetone, it is of 20 ppm (always referred to the carboxylate).

The 83% is therefore recovered of that portion of platinum, which would be lost without the treatment with acetone.

The analysis of the reaction product, carried out by means of the techniques mentioned, showed that the propoxylated-ethoxylated reactant is completely converted into the sodium salt of the related carboxylic acid:

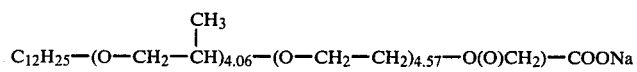

whilst the only propoxylated reactant remains unchanged.

EXAMPLE 28

To a stainless steel autoclave are charged: 710 g of water, 7.65 g of a catalyst of platinum supported on charcoal with 5% of platinum, and 78 g of the hydroxylated reactant:

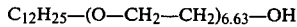

The reaction vessel is purged with nitrogen, and the temperature is raised to 50° C. After having displaced the nitrogen with oxygen, the autoclave is connected to a cylinder, of known volume, provided with precision pressure gauge, and containing oxygen. By means of a pressure reducer, the pressure inside the autoclave is fixed at 4 abs. atm, and the stirring is started.

The pH is controlled within the range of from 7.7 to 8.7 by feeding a solution of 3M sodium hydroxide, by means of a metering pump. The consumption of oxygen is detected from the pressure decrease inside the oxygen cylinder.

After 4 hours of reaction, the absorption of oxygen ends. The reaction mixture is treated as described in Example 1, and the product of reaction is recovered:

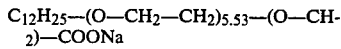

A total conversion is determinated of the hydroxylated reactant and a stoichiometric consumption of oxygen and of sodium hydroxide.

EXAMPLE 29

Inside a glass flask of 1,000 ml, provided with loading funnel, electrode for pH measuring, turbine stirrer with internal gas recycle, nitrogen inlet, inlet for air, metered by a rotameter, and venting system for the defoaming, 300 g of water, 10.3 g of a catalyst of platinum supported on charcoal with 5% by weight of platinum and 40 g of the hydroxylated reactant:

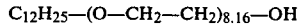

are charged.

After nitrogen purging, the temperature in the flask is raised to 55° C. The nitrogen is displaced with air, and the stirrer is started. In the mean time, a flow is fed of air of 10 Nl/hr, measured by means of the rotameter. The pH is maintained within the range of values of from 7.7 to 8.7 by delivering a 3M solution of sodium hydroxide, stored within the loading funnel.

After 5 hours of reaction at 55°–60° C., the pH is stabilized, and the consumption of sodium hydroxide is equal to the theoretical value.

The reaction mixture is treated in a similar way as in Example 1, and the reaction product is recovered:

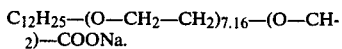

The hydroxylated reactant is completely reacted. The alkali metal salt of polyethoxycarboxylic acids, obtained by means of the process of the present invention, are particularly useful and efficacious for the recovery of crude oil from wells of salinity from medium to high, by means of the Micellar Polymer Flooding. According to the conditions of the particular oil bedding, the surfactants are "built" which allow the most efficacious mobilization of the oil.

According to the technical and patent literature relating to this particular field (D. Balzer, K. Kosswig, "Tenside Detergents" 16 (5), 1979, pages 256–61; D. Balzer, "2nd Europ. Symposium on EOR" (Paris); H. R. Kraft, G. Pusch "SPE/DOE", No. 10714; C. Marx, "BMTF-FB" (1978); European Patent Application publication No. 47369 and No. 47370) the main criterion for the choice of the surfactant consists in the measuring of the phase inversion temperature (PIT), i.e., of the temperature at which a ternary mixture, usually consisting of the water and of the oil of the bedding, and of the surfactant, having a certain composition, and under strong stirring, passes from a state of electrical conductivity to a practically zero conductivity. The determination of the PIT, carried out with the surfactants produced by means of the process of the present invention, was effected with the aid of an AMEL, Model 123 conductimeter, a conductimetric cell with a constant of 1, and a thermostatic bath with temperature programmed and increasing from 20° to 100° C. The mixture on which the measurement is carried out, is formed by the water of the well being examined, by stock tank oil from the same well, and by the surfactant being examined in a weight ratio of 50:50:2 to each other.

With water with total salt content of 15% by weight, and with an oil of naphtenic-aromatic character (well of Cortemaggiore), the surfactant:

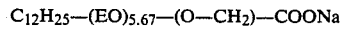

prepared as described above, produces a PIT value of 60° C., which renders the same surfactant particularly suitable for the displacement of the oil in wells having temperatures around 50°–60° C.

The alkaline salts of polyethoxycarboxylic acids, obtained according to the process of the present invention, show a particular thermal stability under conditions of even high salinity, which renders them particularly suitable for the tertiary recovery of the crude oil from beddings with high salt contents.

The tests carried out with the surfactant $$C_{12}H_{25}(EO)_{5.96}—(O—CH_2)—COONa$$

prepared as previously described, effected by dissolving 10% by weight of the surfactant in an aqueous solution of a well with total salinity of 15%, within containers of unactinic glass filled under nitrogen, have shown that the product is particularly stable both at 55° C. and at 85° C. From the analysis of the free alcohol, carried out by NMR analysis, a decomposition percentage is indeed detected lower than 2% after 4 months at 85° C.

Under the same conditions, ethoxylate-sulphonates, with the structure:

$$i—C_{13}H_{27}—O—(EO)_n—CH_2—CHOH—CH_2SO_3Na$$

with n ranging from 3 to 5, show definitely higher degrees of hydrolysis, of the order of 5% after 2 months at 85° C., whilst ethoxylate-sulphate surfactants, with structure $$C_9H_{19}C_6H_4—O—(EO)_n—SO_3Na$$

with n equal to either 10 or 25, reach hydrolysis levels of the order of from 55 to 75% after 2 months at 85° C.

EXAMPLE 30

Example 15 is repeated, operating under the same conditions, but interrupting the reaction when the consumptions of oxygen and of sodium hydroxide are of 80% of the theoretical value. The reaction time is of 3 hours. The analysis (by NMR, TLC) of the reaction mixture shows the presence of only unconverted ethoxylated alcohol (20% molar relative to the charge), together with an 80% molar of carboxylated produced, always evaluated relative to the charge.

TABLE 1

(First Part)

| Example No | Substrate | Load, g $H_2O$ | Load, g 5% of Pt on C | Load, g Substrate | Reaction temperature (°C.) | Reaction time (hours) | Substrate conversion (%) |
|---|---|---|---|---|---|---|---|
| 4 | $C_2H_5—EO_2—OH$ | 350 | 9 | 27 | 50 | 0.75 | 91.8 |
| 5 | $C_6H_{13}—EO_{4.65}—OH$ | 1,420 | 13.6 | 150 | 50–65 | 3.5 | 100 |
| 6 | $C_8H_{17}—EO_{5.62}—OH$ | 1,420 | 12.8 | 150 | 60 | 4 | 100 |
| 7 | $C_{10}H_{21}—EO_{5.85}—OH$ | 1,420 | 13.3 | 150 | 54–63 | 5 | 100 |
| 8 | $C_{12}H_{25}—EO_5—OH$ | 490 | 7.5 | 50 | 50 | 12 | 100 |
| 9 | $C_{12}H_{25}—EO_6—OH$ | 485 | 14.2 | 35 | 50 | 4 | 100 |
| 10 | $C_{12}H_{25}—EO_7—OH$ | 540 | 15.4 | 50 | 50 | 3 | 100 |
| 11 | $C_{12}H_{25}EO_8—OH$ | 1,420 | 12.2 | 150 | 50 | 14 | ~100 |
| 12 | $C_{12}H_{25}EO_9—OH$ | 700 | 11.2 | 75 | 50 | 5 | 100 |
| 13 | $C_{12}H_{25}—EO_{10}—OH$ | 450 | 14.7 | 30 | 50 | 2.5 | 100 |
| 14 | $C_{12}H_{25}—EO_{13}—OH$ | 490 | 14.5 | 50 | 60–65 | 4 | 100 |
| 15 | $C_{12}H_{25}—EO_{11.74}—OH$ | 1,420 | 11.7 | 150 | 50 | 7 | 100 |
| 16 | $C_{12}H_{25}—EO_{15.33}—OH$ | 1,420 | 11.7 | 150 | 50 | 10 | ~100 |
| 17 | $C_{12-13}H_{25-27}—EO_{6.79}—OH$ (1) | 1,420 | 13 | 150 | 50 | 11 | 100 |
| 18 | $C_{12-13}H_{25-27}—EO_{8.99}—OH$ (2) | 1,100 | 19.9 | 100 | 50 | 7 | 100 |
| 19 | $C_{12-15}H_{25-31}—EO_{4.76}—OH$ (3) | 1,200 | 7.8 | 125 | 50–55 | 14 | 100 |
| 20 | $C_{14-15}H_{29-31}—EO_{8.50}—OH$ (4) | 1,420 | 16.1 | 150 | 50 | 7 | 100 |
| 21 | $C_{14}H_{29}—EO_{8.07}—OH$ | 1,420 | 17.0 | 150 | 50 | 7 | 100 |
| 22 | $C_{15}H_{31}—EO_4—OH$ | 350 | 10.6 | 40.7 | 50–70 | 6.5 | 100 |
| 23 | $p-(CH_3)_3CCH_2CH(CH_3)_2C_6H_4EO_{5.41}—OH$ | 1,420 | 10.7 | 150 | 40–60 | 25 | ~100 |
| 24 | $p-(CH_3)_3CCH_2CH(CH_3)_2C_6H_4EO_{7.3}—OH$ | 1,420 | 15 | 150 | 40–50 | 12 | ~100 |
| 25 | $p-(CH_3)_3CCH_2CH(CH_3)_2C_6H_4EO_{9.48}—OH$ | 1,420 | 11 | 150 | 40–60 | 16 | ~100 |
| 26 | $C_{12}H_{25}EO_{6.63}—OH$ | 305 | 15.1 | 75 | 60 | 6 | 100 |

(Second Part)

| Example No | Product obtained Formula | % of theoretical | Purity % | Consumption, % of theoretical value NaOH | Consumption, % of theoretical value $O_2$ |
|---|---|---|---|---|---|
| 4 | $C_2H_5—EO—O—CH_2COONa$ | 93 | 97.4 | 100 | 103 |
| 5 | $C_6H_{13}—EO_{3.65}—O—CH_2COONa$ | 98.6 | >99 | 99.4 | 100.9 |
| 6 | $C_8H_{17}—EO_{4.62}—O—CH_2COONa$ | n.d. | >99 | 99.9 | 100.4 |
| 7 | $C_{10}H_{21}—EO_{4.85}—O—CH_2COONa$ | 102.3 | >99 | 100 | 101.3 |
| 8 | $C_{12}H_{25}—EO_4—O—CH_2COONa$ | 101 | >99 | 105 | n.d. |
| 9 | $C_{12}H_{25}—EO_5—O—CH_2COONa$ | 97.9 | >98 | 100.8 | 100.2 |
| 10 | $C_{12}H_{25}—EO_6—O—CH_2COONa$ | 96.9 | >99 | 105.6 | 107.1 |
| 11 | $C_{12}H_{25}—EO_7—O—CH_2COONa$ | n.d. | >99 | 103.5 | 102.7 |
| 12 | $C_{12}H_{25}—EO_8—O—CH_2COONa$ | n.d. | >99 | 103.7 | 99.2 |
| 13 | $C_{12}H_{25}—EO_9—O—CH_2COONa$ | 93.6 | >99 | n.d. | 100 |
| 14 | $C_{12}H_{25}—EO_{12}—O—CH_2COONa$ | 95.7 | >99 | n.d. | n.d. |
| 15 | $C_{12}H_{25}—EO_{10.74}—O—CH_2COONa$ | n.d. | >99 | 103.2 | 102.7 |
| 16 | $C_{12}H_{25}—EO_{14.33}—O—CH_2COONa$ | n.d. | >99 | 105.4 | 101.4 |
| 17 | $C_{12-13}H_{25-27}—EO_{5.79}—O—CH_2COONa$ | n.d. | >99 | 98.4 | n.d. |
| 18 | $C_{12-13}H_{25-27}—EO_{7.99}—O—CH_2COONa$ | 96.4 | >99 | 101.6 | 104.0 |
| 19 | $C_{12-15}H_{25-31}—EO_{3.76}—O—CH_2COONa$ | 97.7 | >99 | 100.8 | 100.5 |
| 20 | $C_{14-15}H_{29-31}—EO_{7.50}—O—CH_2COONa$ | 97.4 | >99 | 99.5 | n.d. |
| 21 | $C_{14}H_{29}—EO_{7.07}—O—CH_2COONa$ | 99.0 | >99 | 101.8 | 100.1 |

TABLE 1-continued

| | | | | | |
|---|---|---|---|---|---|
| 22 | $C_{15}H_{31}-EO_3-O-CH_2COONa$ | n.d. | >99 | n.d. | n.d. |
| 23 | p-$(CH_3)_3CCH_2CH(CH_3)_2C_6H_4-EO_{4.41}-O-CH_2COONa$ | n.d. | 99 | 101.3 | n.d. |
| 24 | p-$(CH_3)_3CCH_2CH(CH_3)_2C_6H_4-EO_{6.3}-O-CH_2COONa$ | n.d. | 99 | 103.3 | 96.9 |
| 25 | p-$(CH_3)_3CCH_2CH(CH_3)_2C_6H_4-EO_{8.48}-O-CH_2COONa$ | n.d. | 99 | 104.6 | 95.2 |
| 26 | $C_{12}H_{25}-EO_{5.53}-O-CH_2COONa$ | n.d. | 99 | 105.8 | 107.9 |

We claim:

1. In a process for preparing a surfactant agent consisting of an alkaline metal salt of a polyethoxycarboxylic acid having the formula $R'(OR)_m(OCH_2CH_2)_{n-1}(OCH_2)COOM$, in which $R'$ represents a linear or branched alkyl group having from 1 to 20 carbon atoms; R represents an alkylene group, linear or branched, having from 3 to 5 carbon atoms; m is zero or a number up to 30; n is a number from 2 to 30; and M represents an alkaline metal, said process comprising the catalytic oxidation with oxygen or a molecular oxygen-containing gas of a polyethoxylic alcohol having the formula $R'(OR)_m(OCH_2CH_2)_nOH$, in which $R'$, R, m and n are the same as defined above, in the presence of a platinum or palladium catalyst, at a temperature in the range from 40° to 80° C. but lower than the cloud point of said alcohol, in an aqueous reaction mixture characterized by a pH within the range from 7.7 to 8.7, said pH being regulated with use of an alkaline metal hydroxide (MOH), wherein said alcohol is substantially stoichiometrically converted to said alkaline metal salt of the corresponding polyethoxycarboxylic acid;

the improvement wherein the catalyst is substantially completely removed from said reaction mixture, to a level of platinum or palladium of 1 to 4 parts per million relative to said alkaline metal salt, and recovered with a catalytic activity equal to that of fresh catalyst by first contacting the spent catalyst in the reaction mixture with gaseous hydrogen to reactivate it, thus forming an insoluble reactivated catalyst fraction suspended in the reaction mixture and a soluble reactivated catalyst fraction dissolved in the reaction mixture; and thereafter separating the suspended catalyst fraction from the reaction mixture, adding 1 to 10 parts, per each part of mixture, of a liquid aliphatic ketone which is a least partially soluble in the reaction mixture to cause the soluble reactivated catalyst fraction to precipitate from the mixture, and separating the precipitated reactivated catalyst fraction from the reaction mixture.

2. A process as claimed in claim 1 wherein in the formulae $R'$ represents a linear or branched chain alkyl group containing from 6 to 20 carbon atoms; R represents isopropylene or isobutylene; m ranges from 0 to 20; n ranges from 2 to 30; and M represents sodium or potassium.

3. A process as claimed in claim 1 wherein the catalyst contains from 1 to 10% by weight of platinum on a support selected from the group consisting of charcoal and alumina.

4. A process as claimed in claim 1 wherein the reaction is carried out under an oxygen pressure or a partial oxygen pressure of from 0.1 to 4 absolute atmospheres.

5. A process as claimed in claim 1 wherein the reaction is carried out with a weight ratio of platinum or palladium to said polyethoxylic alcohol of from 0.002/1 to 0.02/1.

6. A process as claimed in claim 1 wherein the reaction is carried out with a reaction time of from 1 to 10 hours.

7. A process as claimed in claim 1 wherein the process is carried out at room temperature (20°-25° C.), or at temperatures close to room temperature, for a period of time not shorter than the time during which the consumption of hydrogen takes place.

8. A process as claimed in claim 1 wherein acetone is used as the aliphatic ketone in a quantity from 1.2 to 2 parts by weight per each part by weight of the reaction mixture and the separation of the precipitated catalyst is carried out under conditions of room temperature (20°-25° C.), over a period of time not shorter than the time needed for a substantially complete precipitation of the dissolved catalyst to occur.

* * * * *